US008447406B2

(12) United States Patent
Wu et al.

(10) Patent No.: US 8,447,406 B2
(45) Date of Patent: May 21, 2013

(54) MEDICAL METHOD AND DEVICE FOR MONITORING A NEURAL BRAIN NETWORK

(75) Inventors: Jianping Wu, Shoreview, MN (US); Steven L. Jensen, Andover, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 274 days.

(21) Appl. No.: 12/826,172

(22) Filed: Jun. 29, 2010

(65) Prior Publication Data

US 2011/0319962 A1    Dec. 29, 2011

(51) Int. Cl.
*A61B 5/0482*    (2006.01)
*A61N 1/08*    (2006.01)

(52) U.S. Cl.
USPC ............................................. 607/45; 600/544

(58) Field of Classification Search
USPC ..................... 607/45; 600/544, 545
See application file for complete search history.

(56) References Cited

U.S. PATENT DOCUMENTS

| 6,304,775 | B1 | 10/2001 | Iasemidis et al. |
| 7,353,064 | B2 | 4/2008 | Gliner et al. |
| 7,437,196 | B2 | 10/2008 | Wyler et al. |
| 7,483,747 | B2 | 1/2009 | Gliner et al. |
| 2003/0100931 | A1 | 5/2003 | Mullett |
| 2003/0149457 | A1 | 8/2003 | Tcheng et al. |
| 2003/0204219 | A1 | 10/2003 | Gielen |
| 2007/0043401 | A1 | 2/2007 | John |
| 2007/0213785 | A1* | 9/2007 | Osorio et al. .................. 607/45 |
| 2008/0045775 | A1 | 2/2008 | Lozano |
| 2008/0071327 | A1 | 3/2008 | Miesel et al. |
| 2009/0082829 | A1 | 3/2009 | Panken et al. |
| 2009/0083070 | A1 | 3/2009 | Giftakis et al. |
| 2009/0112281 | A1 | 4/2009 | Miyazawa et al. |
| 2010/0106219 | A1 | 4/2010 | Torgerson et al. |

FOREIGN PATENT DOCUMENTS

| EP | 1985230 A1 | 10/2008 |
| WO | 2008109508 A2 | 9/2008 |
| WO | 2009134475 A1 | 11/2009 |

OTHER PUBLICATIONS

Modolo, J. et al. "Using a Virtual Cortical Module Implementing a Neural Field Model to Modulate Brain Rhythms in Parkinson's Disease." Front. Neruoprosth. 2010; 4: 45. (doi:10.3389/fnins.2010.00045).*

Modolo, Julien et al. "Model-driven therapeutic treatment of neurological disorders: reshaping brain rhythms with neuromodulation." Interface Focus 2011; 1, 61-74. (doi: 10.1098/rsfs.2010.0509).*

Tass, P. et al. "Long-term anti-kindling effects of desynchronizing brain stimulation: a theoretical study." Biol. Cybern. 2006; 94, 58-66. (doi: 10.1007/s00422-005-0028-6).*

(Continued)

*Primary Examiner* — Carl H Layno
*Assistant Examiner* — Allen Porter, Jr.
(74) *Attorney, Agent, or Firm* — Shumaker & Sieffert, PA

(57) ABSTRACT

Bioelectrical signals may be sensed within the brain by two or more electrodes to determine characteristics of a function of the brain. The signals obtained by the electrodes may be plotted over time to determine whether the brain function exhibits a normal or an abnormal pattern. If the brain function exhibits an abnormal pattern, an implantable medical device may dynamically determine based on the abnormal pattern and a previously-obtained plot associated with normal brain function, an appropriate electrical stimulation therapy. Application of the appropriate electrical stimulation therapy causes the brain function to shift from the abnormal pattern to the normal pattern.

28 Claims, 7 Drawing Sheets

OTHER PUBLICATIONS

Santaniello, S. et al. "Adaptive feedback control in deep brain stimulation: a simulation study." Proc. 17th Congress of the Int. Federation of Automatic Control, Seoul, Korea, Jul. 6-11, 2008, pp. 11 624-11 629. Laxenburg, Austria: IFAC.*

Schiff, S. et al. "Kalman filter of a model of spatiotemporal cortical dynamics". J. Neural Eng. 2008; 5, 1-8. (doi: 10.1088/1741-2560/5/1/001).*

Popovych, O. et al. "Impact of nonlinar delayed feedback on synchronized oscillators". J. Biol. Phys. 2008; 34, 267-279. (doi: 10.1007/s10867-008-9068-1).*

Notification of Transmittal of the International Search Report and the Written Opinion of the International Searching Authority for corresponding patent application No. PCT/US2011/041785, mailed Aug. 30, 2011, 14 pages.

Tateno et al., "Phase Resetting Curves and Oscillatory Stability in Interneurons of Rat Somatosensory Cortex," Biophysical Journal, vol. 92, Jan. 2007, 13 pages.

Hauptmann et al., "Cumulative and after-effects of short and weak coordinated reset stimulation: a modeling study," Journal of Neural Engineering, vol. 6, Jan. 2009, 13 pages.

Tass, "Desynchronization of brain rhythms with soft phase-resetting techniques," Biological Cybernetics, vol. 87, Feb. 2002, 14 pages.

Zhai et al., "Desynchronization of coupled electrochemical oscillators with pulse stimulations," Physical Review E, vol. 71, Jun. 2005, 4 pages.

Hauptmann et al., "Effectively desynchronizing deep brain stimulation based on a coordinated delayed feedback stimulation via several sites: a computational study," Biological Cybernetics, vol. 93, Sep. 2005, 8 pages.

Tass, "A model of desynchronizing deep brain stimulation with a demand-controlled coordinated reset of neural subpopulations," Biological Cybernetics, vol. 89, Jul. 2003, 8 pages.

Tass, "Desynchronizing double-pulse phase resetting and application to deep brain stimulation," Biological Cybernetics, vol. 85, Apr. 2001, 12 pages.

Hauptmann et al,, "Desynchronizing the abnormally synchronized neural activity in the subthalamic nucleus: a modeling study," Expert Review Medical Devices, Sep. 2007, 18 pages.

Tass, "Effective desynchronization with bipolar double-pulse stimulation," Physical Review E, vol. 66, Sep. 2002, 9 pages.

Tass, "Effective desynchronization with a resetting pulse train followed by a single pulse," Europhysics Letters, vol. 55(2), May 2001, 7 pages.

Popovych et al., "Effective Desynchronization by Nonlinear Delayed Feedback," The American Physical Society, Apr. 2005, 4 pages.

Tass et al., "Obsessive-Compulsive Disorder: Development of Demand-Controlled Deep Brain Stimulation with Methods from Stochastic Phase Resetting," Neuropsychopharmacology, Jul. 2003, 8 pages.

Neiman, "Response clustering in transient stochastic synchronization and desynchronization of coupled neuronal bursters," Physical Review E, vol. 76, Aug. 2007, 10 pages.

Krachkovskyi et al., "Stimulus-locked responses of two phase oscillators coupled with delayed feedback," Physical Review E, vol. 73, Jun. 2006, 18 pages.

Tass et al., "Therapeutic modulation of synaptic connectivity with desynchronizing brain stimulation," International Journal of Psychophysiology, vol. 64, Apr. 2007, 9 pages.

Hauptmann et al., "Therapeutic rewiring by means of desynchronizing brain stimulation," Elsevier, Biosystems, vol. 89, May-Jun. 2007, 9 pages www.sciencedirect.com.

Barnikol et al., "Tremor entrainment by patterned low-frequency stimulation," Philosophical Transactions of the Royal Society A, Mathematical, Physical & Engineering Sciences, Oct. 2009, 30 pages.

Tass et al., "Long-lasting desynchronization in rat hippocampal slice induced by coordinated reset stimulation," Physical Review E, vol. 80, Jul. 2009, 4 pages.

Tass et al., "Long-term anti-kindling effects of desynchronizing brain stimulation: a theoretical study," Biological Cybernetics, vol. 94, Jan. 2006, 9 pages.

Popovych et al., "Impact of Nonlinear Delayed Feedback on Synchronized Oscillators," Journal of Biological Physics, vol. 34, May 2008, 13 pages.

Majtanik et al., "Desynchronization in Networks of Globally Coupled Neurons with Dendritic Dynamics," Journal of Biological Physics, vol. 32, Nov. 2006, 27 pages.

Popovych et al., "Control of Neuronal synchrony by nonlinear delayed feedback," Biol. Cybernetics, vol. 95, Apr. 2006, 18 pages.

Omel'chenko et al., "Chimera States: The Natural Link Between Coherence and Incoherence," The American Physical Society, Feb. 2008, 4 pages.

Hauptmann et al., "Control of spatially patterned synchrony with multisite delayed feedback," Physical Review E, vol. 76, Dec. 2007, 6 pages.

Vlachos et al., "Discovering Similar Multidimensional Trajectories," Proceedings of the 18th International Conference on Data Engineering, Feb. 2002, 12 pages.

Patent application entitled Electrical Stimulation Based on Phase Response Mapping, U.S. Appl. No. 12/727,889, filed Mar. 19, 2010, Jensen et al.

* cited by examiner

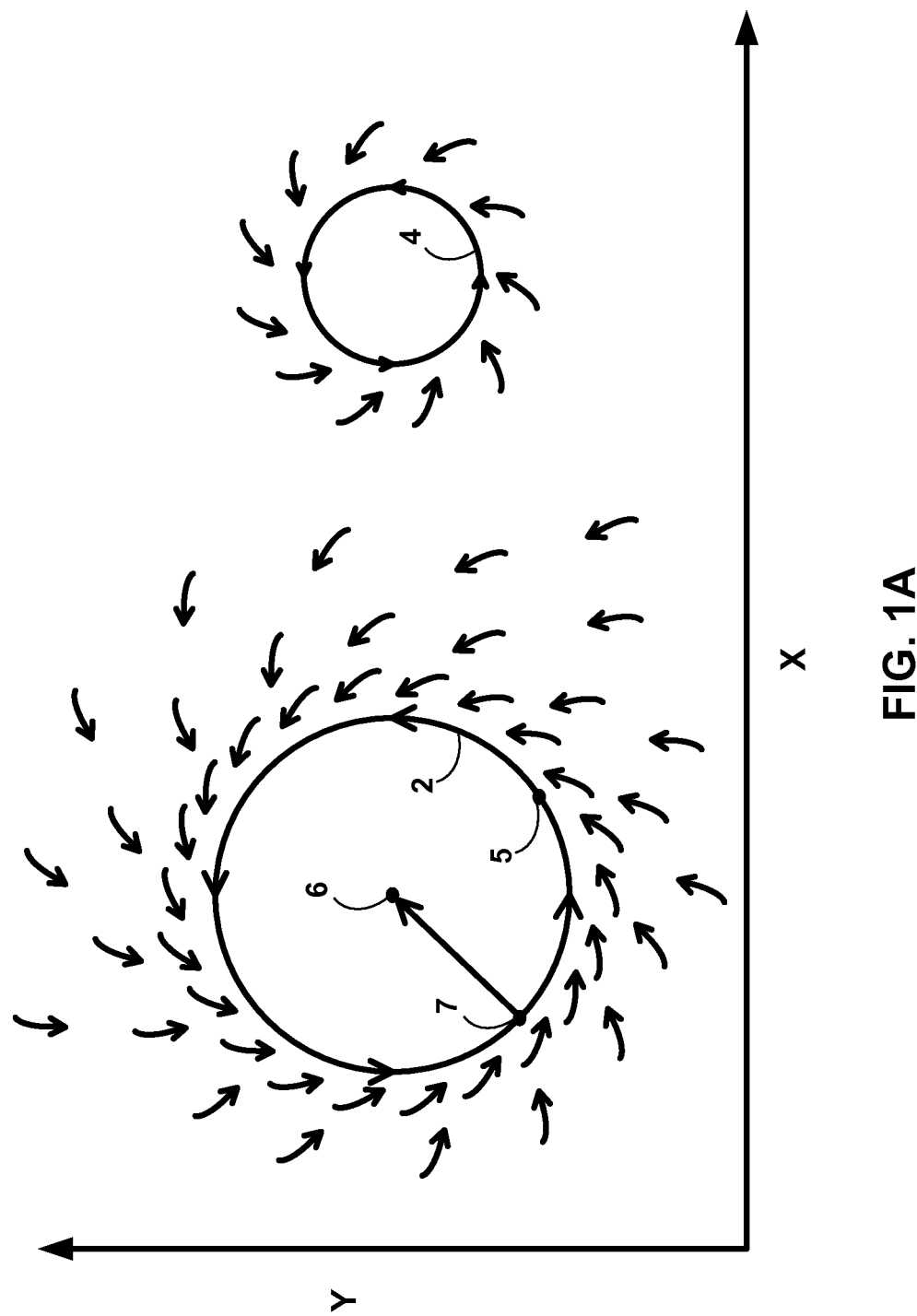

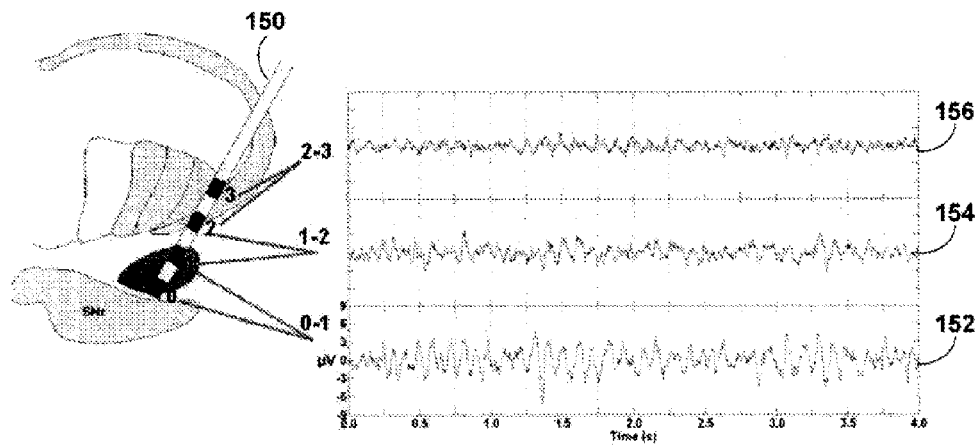
FIG. 1B
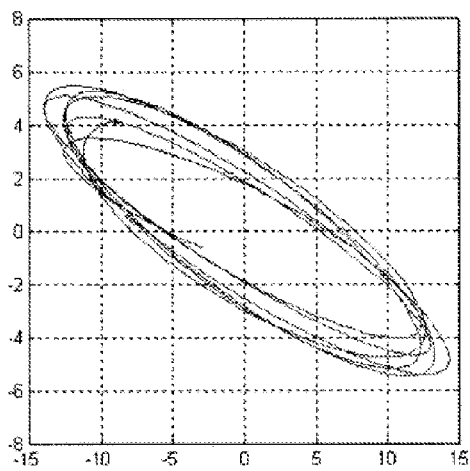 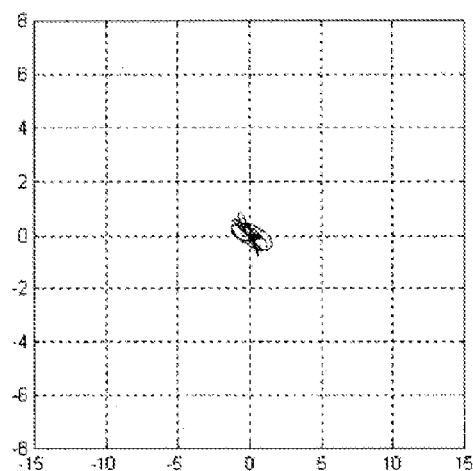
FIG. 1C     FIG. 1D

ND DEVICE FOR
MEDICAL METHOD AND DEVICE FOR MONITORING A NEURAL BRAIN NETWORK

TECHNICAL FIELD

The disclosure relates to medical therapy systems, and, more particularly, control of medical therapy systems.

BACKGROUND

Implantable medical devices, such as electrical stimulators, may be used in different therapeutic applications. In some therapy systems, an implantable electrical stimulator delivers electrical therapy to a target tissue site within a patient with the aid of one or more medical leads that include electrodes. In addition to or instead of electrical stimulation therapy, a medical device may deliver a therapeutic agent to a target tissue site within a patient with the aid of one or more fluid delivery elements, such as a catheter.

Implantable medical devices, such as electrical stimulators, may target, for example, neurological disorders that include movement disorders, such as tremor, Parkinson's disease, multiple sclerosis, or spasticity. Implantable medical devices may also monitor functions of the organs with which they are associated, such as, for example, the functions of the brain. Monitoring functions of the organs targeted by an implantable medical device may support delivery of more effective therapy stimulation. In some cases, particularly with neurological and brain-related disorders and functions, abnormalities may be difficult to detect and distinguish from normal functionalities.

SUMMARY

In general, the disclosure is directed to techniques for monitoring a neural brain network to detect abnormal or undesired brain signal oscillatory behavior. In some cases, the detected oscillatory behavior may be used to control an electrical stimulation device to deliver electrical stimulation to a brain of a patient to condition brain functions. In some examples, the electrical stimulation may be configured to support and/or abolish neural oscillatory behavior within the brain neural network. An implanted electrical stimulation device may sense brain signals to determine oscillatory behavior associated with the neural activities linked to a particular condition, e.g., Parkinson's disease (PD). Using a known normal behavior associated with the neural activity, the implanted device may utilize the determined oscillatory behavior to apply appropriate stimulation therapy, such that the behavior of the neural activity resembles that of the normal behavior. In one example, the normal behavior may be a stable behavior of the neural activity associated with the application of a drug for the particular condition, e.g., dopamine for PD.

In one example, the disclosure is directed to a method comprising sensing at least two bioelectrical signals within a brain of a patient using at least two implantable electrodes of a medical device, determining based on the at least two signals a first state associated with the brain, and adjusting therapy delivered by an implantable medical device based on the first state, wherein the adjustment is selected to, upon application of the adjustment to the therapy, alter the first state to a second state associated with the brain.

In another example, the disclosure is directed to an implantable medical device comprising at least two implantable electrodes that sense at least two bioelectrical signals within a brain of a patient, and a processor that determines based on the at least two signals a first state associated with the brain, and adjusts therapy delivered by the implantable medical device based on the first state, wherein the adjustment is selected to, upon application of the adjustment to the therapy, alter the first state to a second state associated with the brain.

In another example, the disclosure is directed to a computer-readable medium comprising instruction that, upon execution, cause a processor to analyze at least two bioelectrical signals within a brain of a patient sensed via at least two implantable electrodes of a medical device, determine based on the at least two signals a first state associated with the brain, and adjust therapy delivered by an implantable medical device based on the first state, wherein the adjustment is selected to, upon application of the adjustment to the therapy, alter the first state to a second state associated with the brain.

In another example, the disclosure is directed to a device comprising means for sensing at least two bioelectrical signals within a brain of a patient using at least two implantable electrodes of a medical device, means for determining based on the at least two signals a first state associated with the brain, and means for adjusting therapy delivered by an implantable medical device based on the first state, wherein the adjustment is selected to, upon application of the adjustment to the therapy, alter the first state to a second state associated with the brain.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIG. 1A illustrates an exemplary limit cycle plot of a trajectory of a signal observed at location Y versus a signal observed at location X.

FIG. 1B illustrates exemplary signals observed by implanted lead at three different electrode locations.

FIG. 1C illustrates exemplary limit cycle plot of a trajectory of a signal observed at two locations in a PD patient who has not received medication.

FIG. 1D illustrates exemplary limit cycle plot of a trajectory of a signal observed at the two locations of FIG. 1C in the PD patient who has received medication.

DETAILED DESCRIPTION

Figure 2:
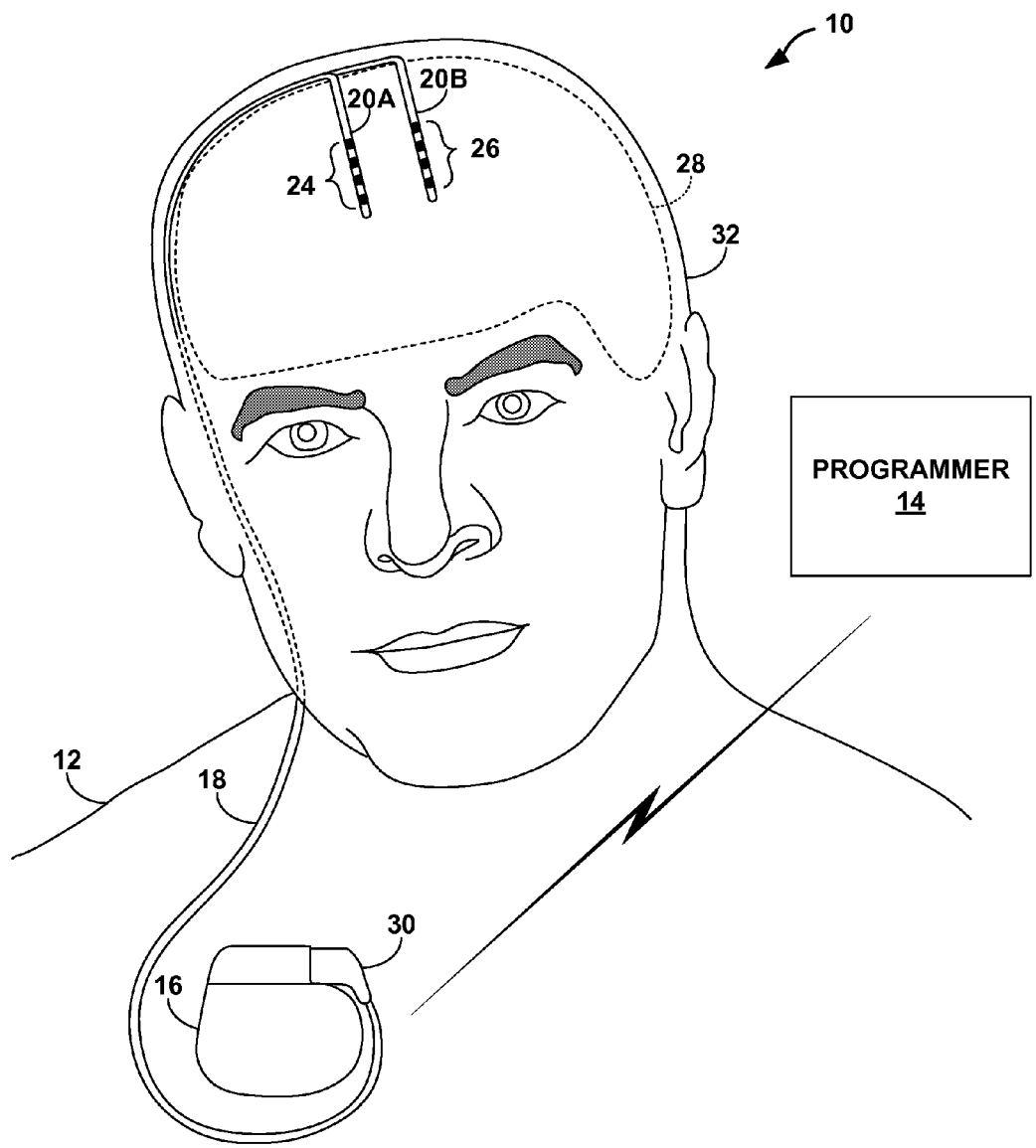
FIG. 2 is a conceptual diagram illustrating example deep brain stimulation (DBS) system.

Neural oscillations may exist temporally and spatially within neural brain networks, whether the brain is exhibiting normal functions or whether some abnormal activity (e.g., activity associated with neural disorders) is occurring. Therefore, neural oscillatory activity may be measured in certain areas of the brain, and may be used to monitor functions of the brain. Certain abnormal functions of the brain, such as those associated with some movement disorders (e.g., Parkinson's disease (PD), epilepsy), may result in oscillatory behavior or changes in normally-occurring oscillatory behavior indicative of the presence of the abnormal brain functions and/or indicative of the disorder. Monitoring oscillatory behavior in the brain may be useful in understanding the difference between normal and abnormal brain functions, and therefore, may be useful in identifying abnormal functions and correcting them when present. Observing neural oscillations may be done for monitoring purposes, diagnostic purposes, and/or therapeutic purposes, e.g., in supporting control of delivery of medical therapy such as electrical stimulation.

In general, the disclosure is directed to techniques for monitoring a neural brain network to detect abnormal or undesired oscillatory behavior in brain signals. In some cases, the detected oscillatory behavior may be used to control a therapy-delivery device to deliver therapy to a brain of a patient to condition brain functions. In one example, the detected oscillatory behavior may be used to control an electrical stimulation device to deliver electrical stimulation to the brain of the patient to condition the brain functions associated with the oscillatory behavior. In some examples, the electrical stimulation may be configured to support and/or abolish neural oscillatory behavior within the brain neural network. In another example, the detected oscillatory behavior may be used to control a drug-delivery device to deliver drugs and/or medication to the brain of the patient to condition the brain functions associated with the oscillatory behavior. In this example, the drugs and/or medication therapy may be configured to deliver a specific amount of drugs and/or medication to support and/or abolish neural oscillatory behavior within the brain neural network. While techniques of this disclosure are discussed in terms of electrical stimulation therapy, it should be understood that these techniques can be similarly applicable in configuring and controlling drug-delivery therapy.

An implanted medical device (IMD) that provides electrical stimulation therapy to the patient may be used to sense brain signals to determine oscillatory behavior associated with the neural activities linked to a particular condition, e.g., PD and epilepsy. Using a known normal behavior associated with the neural activity, the implanted device may utilize the determined oscillatory behavior to apply appropriate therapy (e.g., electrical stimulation therapy or drug-delivery therapy), such that application of the therapy changes the behavior of the neural activity and alters it until it resembles that of the normal behavior. In one example, the normal behavior may be a stable behavior of the neural activity associated with the application of a drug for the particular condition, e.g., dopamine for PD. In another example, the normal behavior may be a stable behavior of the neural activity associated with the patient when not exhibiting symptoms of the disorder or reduced symptoms, e.g., when patient is not experiencing an epileptic seizure. While a disorder may generally exhibit a certain behavior, sensed signals used to determine the exact behavior may differ from one patient to another based on anatomy, location of the device used to sense the signals, the severity of the patient's condition, and the like. Aspects of this disclosure ensure that determinations regarding the behavior of neural activity are patient-specific, and determination of therapy is therefore also patient-specific and can dynamically adapt to system changes such as, for example, a migration in stimulation electrode implant location, changes in the severity of the disorder, and the like.

In some examples, two or more lead electrodes may be utilized to obtain two or more bioelectrical signals associated with neural activity. A limit cycle plot (a plot showing the trajectory of two or more variables overtime, i.e., the path of two or more variables as time approaches infinity) of the signals may be obtained and analyzed to determine the oscillatory behavior of the neural activity of the associated brain network. If the signals are obtained during a normal or stable state (e.g., during a period when it is known that there are no abnormal functions associated with the brain), the plot of the neural brain signals may be stored for future comparisons to determine whether a neural brain network is functioning normally or to provide appropriate therapy when abnormal behavior is sensed. If the signals are obtained during an abnormal state (e.g., during a period when the patient is showing signs of an abnormal state such as tremor or rigidity for a patient with PD or during a seizure for an epileptic patient), the plot of the neural brain signals may be compared to a plot of the neural brain signals for a normal or stable behavior to determine characteristics of the abnormal behavior and to select an appropriate therapy to restore the behavior back to the normal or stable state or near-normal state. Additionally, having knowledge of the patterns associated with a normal state of neural activity of the brain network along with some knowledge of patterns associated with an abnormal state or knowledge of the acute or long term changes in patterns associated with stimulation or therapy delivery may allow initial programming of stimulation therapy parameters that may shift the abnormal pattern to a pattern associated with a normal or stable state of the neural activity. In one aspect of this disclosure, once an abnormal pattern is detected, an existing program may be selected and dynamically adjusted according to the characteristics of the detected abnormal pattern of the neural activity, such that application of the adjusted program shift the neural activity to a normal or stable pattern or pattern that is more approximating of normal or a pattern associated with successful therapeutic effects based upon other patient symptoms.

In some examples, the abnormal oscillatory behavior may be somewhat continuous for certain disorders, unless therapy is provided. For example, a patient with PD may have a continuous tremor or rigidity unless therapy is provided, e.g., a dose of dopamine or appropriate neurostimulation delivery. In this example, to determine characteristics of normal or stable behavior of the neural activity, the patient may receive a dose of dopamine to stabilize an abnormal condition associated with PD, e.g., tremor or rigidity, and then observe the oscillatory behavior of the neural activity to determine characteristics of the normal/stable behavior. In other examples, the abnormal oscillatory behavior may occur infrequently or intermittently for certain disorders. For example, a patient suffering from epilepsy may experience seizures sporadically, while exhibiting a normal or stable condition otherwise. In this example, to determine the characteristics of normal or stable behavior of neural activity, the patient may be observed any time while not experiencing a seizure and a signal may be obtained over time as long as the patient is exhibiting a normal or stable state. The signal obtained during the normal or stable state may be used to determine the normal or stable pattern of the signal for future assessment of the patient.

In some examples, the device may monitor oscillations within a neural brain network as they form and subside such as, for example, during onset/offset of drug therapy, neurostimulation, or associated movement or cognitive events. The trajectory of the plot of the monitored oscillations may enable monitoring and understanding of normal/stable states and abnormal/unstable states within the neural brain network. In one example, the device may apply signal analysis algorithms that analyze patterns of monitored oscillations of a neural brain network activity to determine the appropriate therapy to abolish or establish oscillatory patterns or frequency ranges, depending on characteristics of a normal or stable state of a neural network, as explained in more detail below. The IMD may deliver stimulation to alter the state from an abnormal state to a normal state. The stimulation (e.g., electrical stimulation or drug delivery) may be continuous, intermittent series of stimulations, or a single electrical pulse or drug dose. The effects of timing and characteristics of the stimulation (e.g., intensity, amplitude, duration, pulse width, frequency, and the like) relative to the oscillations of the neural brain network activity may be monitored. In some examples, the abnormal state may exhibit oscillatory behavior, and the normal state may be a fixed or stable point. In other examples, the abnormal state may exhibit oscillatory behavior at a first frequency, and the normal state may exhibit oscillatory behavior at a second frequency. Knowledge of the normal or stable behavior may allow the IMD to select and deliver the appropriate amount of stimulation to shift the neural activity pattern from the abnormal state to the normal or stable state.

FIG. 1A illustrates an exemplary limit cycle plot of a trajectory of a signal observed at location Y versus a signal observed at location X. In one example, locations X and Y may represent the locations of two electrodes that are spatially distinct. Electrodes X and Y may be utilized to sense a signal over a period of time and provide measurements associated with the sensed signal. The sensed signals may be measured using, for example, amplitude of a voltage level, a frequency, or the like. In some examples, measurements may represent measurements of concentrations of chemicals in the brain. Hence, values presented in FIG. 1A may represent voltage level, frequency, or other parameters of the sensed signals. For example, FIG. 1A may illustrate a plot of voltage amplitude of the signal sensed via the X electrode versus voltage amplitude of the signal sensed via the Y electrode. In other words, the X axis may indicate the X electrode amplitude (or phase, or other parameter), and the Y axis may indicate the Y electrode amplitude (or phase, or other parameter). As the signals at X and Y are observed over time, the values associated with X and Y are plotted, where the value associated with Y is plotted versus the value associated with X that is observed at the same instant in time. The same process may be repeated for different states of the neural activity to better understand the neural activity behavior associated with different states of a patient's condition, e.g., abnormal and normal/stable behavior. The plot of Y versus X may be used to determine the characteristics of the behavior of the neural activity. In the example of FIG. 1, the observed behavior for one state, e.g., an abnormal state, may take an identifiable shape such as, for example, a circle 2. It should be understood that the shapes used in this example are illustrative, and that the plot may take any shape. Referring to FIG. 1A, if the behavior of the neural activity falls into a pattern that looks like or that falls on circle 2, then the neural activity indicates presence of an abnormal behavior, e.g., tremor or rigidity in the example of PD or seizure in the example of epilepsy. A plot may be also obtained for the neural activity at a second state such as, for example, a normal or stable state. In one example, the normal state behavior may be a fixed stable point, e.g., point 6, or it may be another pattern, e.g., circle 4. While the neural activity exhibits an abnormal behavior, i.e., on circle 2, the IMD may provide variable stimulation (e.g., at different timings in terms of location on circle 2, different stimulation parameter values) to determine how application of different stimulations affects the neural activity behavior, and the observed behavior may be also measured by electrodes X and Y and plotted.

Referring to FIG. 1A, the behavior resulting from the variable stimulation parameters applied by the IMD may be represented by the small arrows, where an arrow may indicate the location to which the observed signal jumps upon applying stimulation, and the direction the signal tends following stimulation application. In this manner, the arrows may represent the result of the stimulation adjustment on the oscillatory behavior of the signals sensed via the X and Y electrodes. For the majority of the points on circle 2, when stimulation is applied, the signal representing the neural activity exhibits behavior outside the abnormal state, i.e., not on circle 2, but eventually returns to circle 2 (it should be noted that there is an infinite number of points and arrows that represent the different combinations of applied stimulation to the point on circle 2, and the few shown arrows are illustrative). However, at certain points, when the appropriate amount of stimulation is applied at an appropriate time (i.e., at the appropriate location on circle 2), the neural activity may shift from the abnormal state to a normal or stable state.

For example, if the normal or stable state of a certain condition is a fixed stable point, e.g., point 6, when the IMD selects and applies the appropriate stimulation at the appropriate time, the neural activity shifts from the abnormal state of being on circle 2 to the normal or stable state of being at point 6. In this example, the appropriate time may be point 7 on circle 2, and selection of the appropriate stimulation may cause the neural activity to shift to point 6, therefore, stabilizing the abnormal behavior of the neural activity and shifting it to a normal state. In another example, the normal or stable state may be another oscillatory state, e.g., circle 4. In this example, the appropriate time may be point 5 on circle 2, and the appropriate stimulation may cause the neural activity to shift to circle 4 or to a point near circle 4 such that, when the neural activity is shifted to such a point (e.g., points represented by the arrows around circle 4), the neural activity will eventually get to circle 4. In this example, the applied stimulation may be one or more electrical pulses applied until the neural activity pattern shifts to the normal or stable pattern. In the example where applying the stimulation shifts the neural activity behavior from an abnormal oscillatory state (circle 2) to a normal oscillatory state (circle 4), the applied stimulation may be shifting the signal of the neural behavior from a low frequency path or rhythm to a high frequency path or rhythm. In other examples, the normal oscillatory state may exhibit the lower frequency behavior, and application of the appropriate stimulation may shift the signal from a high frequency path (e.g., circle 4) to a lower frequency path (e.g., circle 2).

FIG. 1B illustrates exemplary signals observed by implanted lead 150 at three different electrode locations. In this example, lead 150 may be implanted in the subthalamic nucleus (STN) in the brain of a patient with PD. Lead 150 may comprise a plurality of electrodes such as, for example, electrodes 0-3. In one example, pairs of electrodes may be utilized to sense a signal over a period of time and provide measurements associated with the sensed signal. In this example, the pairs of electrodes may be electrodes 0 and 1, 1 and 2, and 2 and 3. The signals may be sensed from the STN of the patient and recorded over time as illustrated in FIG. 1B. In this example, the measurement may be amplitude of the signal in micro volts ($\mu V$). Plot 152 may represent the signal observed by the pair of electrodes 0 and 1, plot 154 may represent the signal observed by the pair of electrodes 1 and 2, and plot 156 may represent the signal observed by the pair of electrodes 2 and 3. In one example, two or more of plots 152, 154, and 156 may be utilized to better understand the behavior of neural activity associated with PD in this particular patient. For example, if using two of the observed signals, a user may select the signals that correspond to plots 152 and 156, as plots 152 and 156 correspond to signals obtained by electrodes that are more spatially distinct.

FIG. 1C illustrates an exemplary limit cycle plot of a trajectory of a signal observed at two locations in a PD patient who has not received medication. In this example, the amplitudes of the signal corresponding to plot 156 versus the signal corresponding to plot 152 may be plotted, where the amplitude associated with electrodes 2 and 3 (y-axis) is plotted versus the amplitude associated with electrodes 0 and 1 (x-axis) that is observed at the same instant in time. The example plot of FIG. 1C illustrates the behavior of neural activity observed at the STN of a patient with PD during a time when the patient may not be receiving medication and is experiencing abnormal neural behavior associated with PD. As FIG. 1C illustrates, abnormal behavior associated with PD may exhibit oscillatory behavior with a somewhat circular pattern, as shown.

FIG. 1D illustrates exemplary limit cycle plot of a trajectory of a signal observed at the two locations of FIG. 1C in the PD patient who has received medication. In this example, the amplitude associated with electrodes 2 and 3 is plotted versus the amplitude associated with electrodes 0 and 1 that is observed at the same instant in time. In this example, the observation may be conducted during a time when the patient is receiving medication and/or neurostimulation that controls abnormal neural activity associated with PD. The example plot of FIG. 1D illustrates the behavior of neural activity observed at the STN of the PD patient when the neural activity is normal or stable. In other words, the behavior of the neural activity of FIG. 1D is the desired or normal or stable neural activity as it should be observed at the STN of the patient, and application of therapy may be designed as to result in neural activity that resembles the neural activity of FIG. 1D.

Using the techniques of this disclosure, signals observed at the STN during abnormal (FIG. 1C) and normal (FIG. 1D) neural activity may be utilized to determine an appropriate therapy, where application of the therapy alters neural activity behavior from the abnormal state to the normal state. In one example, the appropriate therapy may be electrical stimulation configuration, which may be applied by an IMD, such that whenever the neural activity starts exhibiting an abnormal behavior, the IMD applies the appropriately-configured stimulation to alter the neural activity back to the normal or stable behavior, as illustrated in FIG. 1D.

It should be understood that while this disclosure illustrates and discusses examples where two electrodes are used to sense signals of neural activity, two or more electrodes may be utilized to sense the signals. For example, three spatially-distinct electrodes may be utilized and the resulting trajectory plot may be 3-dimensional, and so forth.

FIG. 2 is a conceptual diagram illustrating an example deep brain stimulation (DBS) system 10 that manages a medical condition of patient 12. The medical condition may be, for example, a movement disorder, neurodegenerative impairment, a mood disorder, or a seizure disorder of patient 12. While movement disorders and neurodegenerative impairment are primarily referred to herein, in other examples, therapy system 10 may provide therapy to manage symptoms of other patient conditions, such as, but not limited to, seizure disorders (e.g., epilepsy), mood (or psychological) disorders (e.g., major depressive disorder (MDD), bipolar disorder, anxiety disorders, post traumatic stress disorder, dysthymic disorder, and obsessive-compulsive disorder (OCD)), or Alzheimer's disease.

DBS system 10 includes medical device programmer 14, implantable medical device (IMD) 16, lead extension 18, and lead 20 with respective electrodes 22A and 22B (collectively referred to as "electrodes 22"). Patient 12 ordinarily will be a human patient. In some cases, however, DBS system 10 may be applied to other mammalian or non-mammalian non-human patients. In some examples, some patient conditions, may be detected and abolished by understanding and monitoring the functions and activities of neural networks and brain sites associated with and affected by the conditions. DBS system 10 may provide therapy in order to minimize the severity or duration of the patient condition, and, in some cases, in order to reduce or eliminate symptoms associated with the patient condition.

A movement disorder or other neurodegenerative impairment may include symptoms such as, for example, muscle control impairment, motion impairment or other movement problems, such as rigidity, bradykinesia, rhythmic hyperkinesia, nonrhythmic hyperkinesia, and akinesia. In some cases, the movement disorder may be a symptom of PD. However, the movement disorder may be attributable to other patient conditions. Although movement disorders are primarily referred to throughout the remainder of the disclosure, the therapy systems and methods described herein are also useful for managing (e.g., controlling patient symptoms) other patient conditions, such as neurodegenerative impairment or mood disorders.

Therapy system 10 includes medical device programmer 14, IMD 16, lead extension 18, and leads 20A and 20B with respective sets of electrodes 24, 26. In the example shown in FIG. 2, electrodes 24, 26 of leads 20A, 20B are positioned to deliver electrical stimulation to a tissue site within brain 28, such as a deep brain site under the dura mater of brain 28 of patient 12. In some examples, delivery of electrical stimulation to one or more regions of brain 28, such as the subthalamic nucleus, globus pallidus or thalamus, may be an effective treatment to manage movement disorders, such as Parkinson's disease. Electrodes 24, 26 are also positioned to sense bioelectrical brain signals within brain 28 of patient 12. In some examples, some of electrodes 24, 26 may be configured to sense bioelectrical brain signals and others of electrodes 24, 26 may be configured to deliver electrical stimulation to brain 28. In other examples, all of electrodes 24, 26 may be configured to both sense bioelectrical brain signals and deliver electrical stimulation to brain 28, as needed.

IMD 16 includes a therapy module that includes a stimulation generator that generates and delivers electrical stimulation therapy to patient 12 via a subset of electrodes 24, 26 of leads 20A and 20B, respectively. The subset of electrodes 24, 26 that is used to deliver electrical stimulation to patient 12, and, in some cases, the polarity of the subset of electrodes 24, 26, may be referred to as a stimulation electrode combination or configuration. The subset of electrodes 24, 26 that is used to sense bioelectrical brain signals may be referred to as a sensing electrode combination or configuration.

The stimulation electrode combination can be selected for a particular patient 12 and target tissue site (e.g., selected based on the patient condition and/or a sensed event or activity of the target tissue site) based on one or more frequency domain characteristics of a bioelectrical brain signal that is sensed by one or more groups of electrodes 24, 26 that are associated with the stimulation electrode combination, or the sensing electrode combination. The group of electrodes 24, 26 includes at least one electrode and can include a plurality of electrodes. In some examples, the bioelectrical signals sensed within brain 28 may reflect changes in electrical current produced by the sum of electrical potential differences across brain tissue. Examples of bioelectrical brain signals include, but are not limited to, electrical signals generated from local field potentials (LFP) sensed within one or more regions of brain 28, such as an electroencephalogram (EEG) signal, or an electrocorticogram (ECoG) signal. Local field potentials, however, may include other types of electrical signals within brain 28 of patient 12.

In some examples, the sensing electrode combination may be used to monitor brain neural network activities such as, for example, oscillatory behavior in bioelectrical brain signals. In one example, oscillatory behavior associated with a brain site may be monitored over a certain amount of time to determine whether it exhibits a certain pattern and the characteristics of the pattern. The pattern may indicate that a monitored brain site is functioning in a normal/stable state or in an abnormal/unstable state. In one example, an abnormal/unstable state may be associated with a certain disorder, e.g., PD or epilepsy. Therefore, if an abnormal state is sensed by the sensing electrode combination, a stimulation electrode combination may be used to provide stimulation therapy to put the associated target tissue site back in a normal/stable state that is characteristic of normal neural activity of the associated target tissue site. While the examples of this disclosure are described using two electrodes 24 and 26, more electrodes may be used to monitor and/or provide therapy to restore the activity of a brain neural network to a normal/stable state when an abnormal/unstable state is detected.

Figure 3:
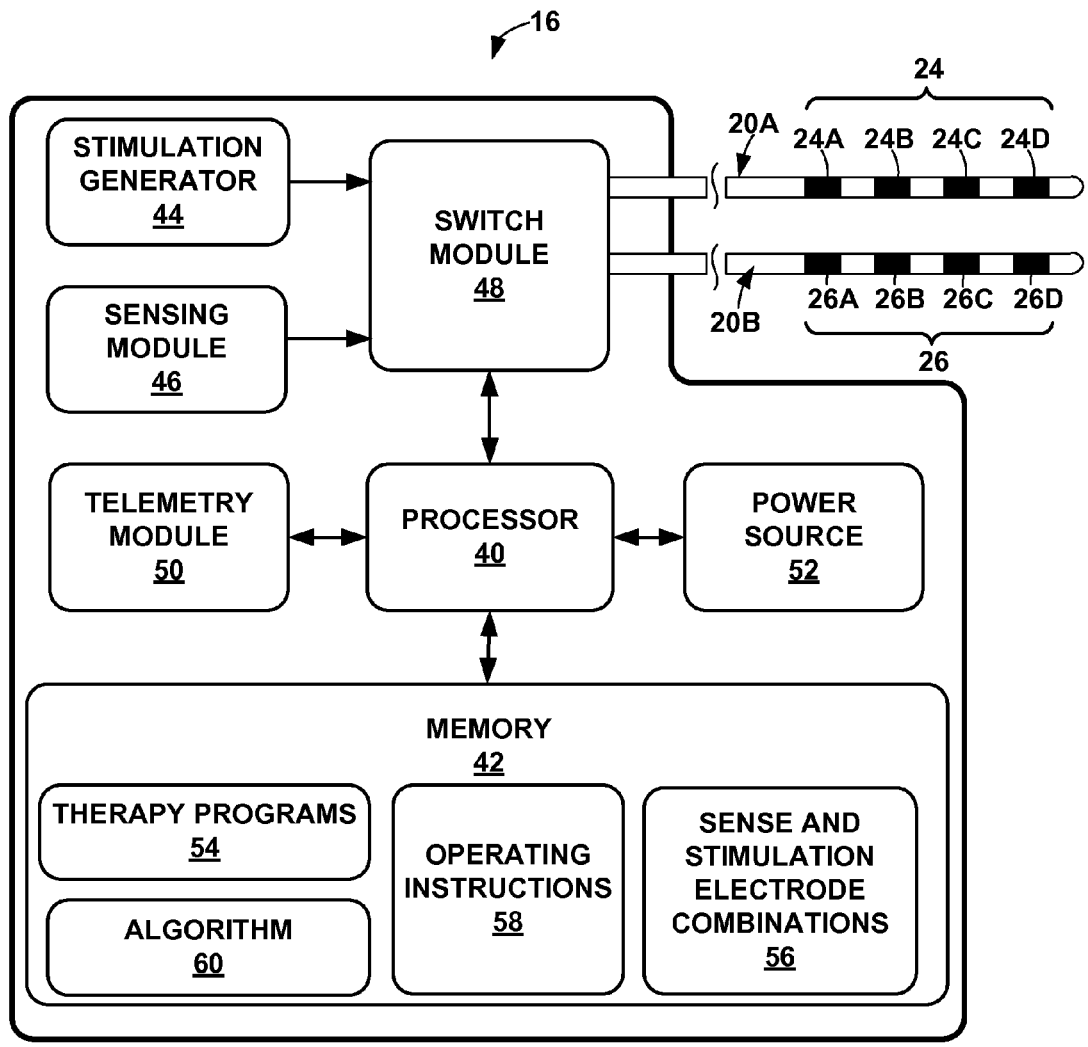
FIG. 3 is functional block diagram illustrating components of an example medical device suitable for use in the DBS system of FIG. 1.

FIG. 3 is a functional block diagram illustrating components of an example IMD 16. In the example shown in FIG. 2, IMD 16 includes processor 40, memory 42, stimulation generator 44, sensing module 46, switch module 48, telemetry module 50, and power source 52. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 40, cause IMD 16 to perform various functions.

In the example shown in FIG. 3, memory 42 stores therapy programs 54, sense electrode combinations and associated stimulation electrode combinations 56, operating instructions 58, and algorithm 60 in separate memories within memory 42 or separate areas within memory 42. In addition, in some examples, memory 42 may store a bioelectrical brain signal sensed via at least some of the stored sense electrode combinations and/or one or more frequency band characteristics of the bioelectrical brain signals. Each stored therapy program 52 defines a particular set of electrical stimulation parameters, such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis. In some examples, therapy programs may define parameters for a therapy that may be applied to shift an activity of a certain site or region in the brain from one state to another, for example, from an abnormal state to a normal/stable. In one example, therapy programs 54 may also include characteristics of expected normal behavior associated with patient disorders and/or conditions.

Sense and stimulation electrode combinations 56 stores sense electrode combinations and stimulation electrode combinations. In some examples, the sense and stimulation electrode combinations may include the same subset of electrodes 24, 26, or may include different subsets of electrodes. Thus, memory 42 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processor 40. In some examples, corresponding sense and stimulation electrode combinations may comprise some or all of the same electrodes. In other examples, however, some or all of the electrodes in corresponding sense and stimulation electrode combinations may be different. In some examples, stimulation may be delivered via a stimulation electrode combination to a tissue site that is different than the tissue site closest to the corresponding sense electrode combination but is within the same region, e.g., the thalamus, of brain 28 in order to mitigate any abnormal behavior or other irregular brain activity within the tissue site associated with the sense electrode combination.

Operating instructions 58 guide general operation of IMD 16 under control of processor 40, and may include instructions for measuring the impedance of electrodes 24, 26 and/or determining the distance between electrodes 24, 26. Algorithm 60 includes instructions for an algorithm that processor 40 may execute in order to determine which electrodes from a sense electrode combination are, for example, closest to or most effective to provide therapy to a target tissue site for stimulation therapy to manage a particular patient. In some examples, algorithm 60 may include instructions executed by the processor 40 to analyze signals sensed of neural activity to determine characteristics of the behavior or the state associated with the neural activity for monitoring and/or therapeutic purposes. Algorithm 60 may include instructions executed by processor 40 to analyze characteristics of a trajectory associated with signals of neural activities measured by the electrodes 24 and 26. In some examples, algorithm 60 may include instructions executed by processor 40 to analyze the trajectory of signals of neural activity of a brain site to determine whether the neural activities are exhibiting normal or abnormal behavior, and to determine an appropriate course of action if an abnormal behavior is detected (e.g., appropriate stimulation therapy), and to instruct the processor to apply the appropriate stimulation to correct any abnormal behavior.

The target tissue site may be, for example, a tissue site within brain 28 that exhibits neural activity with oscillatory behavior. The oscillatory behavior may be determined based on bioelectrical signals measured by the sense electrode combination. For a certain target tissue site, oscillatory behavior may be monitored and obtained when it is known the behavior reflects normal conditions, for example, following administration of medication (e.g., dose of dopamine to a PD patient) or therapy (electrical stimulation to eliminate tremor), or while the patient is known to not be experiencing he disorder (e.g., when an epileptic patient is not experiencing a seizure), and the like. In some examples, deviations from normal oscillatory behavior may be used to characterize disorders and/or deliver effective DBS to restore the system to a normal state by providing therapy that shifts the neural activity from an abnormal state to a normal state.

Stimulation generator 44, under the control of processor 40, generates stimulation signals for delivery to patient 12 via selected combinations of electrodes 24, 26. An example range of electrical stimulation parameters believed to be effective in DBS to manage a movement disorder of patient include:

1. Frequency: between approximately 100 Hz and approximately 500 Hz, such as approximately 130 Hz.
2. Voltage Amplitude: between approximately 0.1 volts and approximately 50 volts, such as between approximately 0.5 volts and approximately 20 volts, or approximately 5 volts.
3. Current Amplitude: A current amplitude may be defined as the biological load in which the voltage is delivered. In a current-controlled system, the current amplitude, assuming a lower level impedance of approximately 500 ohms, may be between approximately 0.2 milliAmps to approximately 100 milliAmps, such as between approximately 1 milliAmps and approximately 40 milliAmps, or approximately 10 milliAmps. However, in some examples, the impedance may range between about 200 ohms and about 2 kilo-ohms.
4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 44 generates electrical stimulation signals in accordance with the electrical stimulation parameters noted above. Other ranges of therapy parameter values may also be useful, and may depend on the target stimulation site within patient 12. While stimulation pulses are described, stimulation signals may be of any form, such as continuous-time signals (e.g., sine waves) or the like. Stimulation generator 44 may shift the delivery of stimulation energy between two therapy programs, and processor 40 of IMD 16 may provide instructions that cause stimulation generator 44 to time-interleave stimulation energy between the electrode combinations of the two therapy programs. Stimulation generator 44 may be voltage-controlled or current-controlled. In one example, a single stimulation generator may be used to interleave or multiplex stimulation across different electrode combinations. In another example, multiple stimulation generators may be coupled to different electrode combinations.

Processor 40 may include any one or more of a microprocessor, a controller, a digital signal processor (DSP), an application specific integrated circuit (ASIC), a field-programmable gate array (FPGA), discrete logic circuitry, and the functions attributed to processor 40 herein may be embodied as firmware, hardware, software or any combination thereof. Processor 40 controls stimulation generator 44 according to therapy programs 54 stored in memory 42 to apply particular stimulation parameter values specified by one or more of programs, such as, for example, amplitude, pulse width, and pulse rate. Processor 40 also controls the selection of the sensing electrode combinations and the monitoring of the target tissue site neural activity to determine the associated oscillatory patterns and state (normal or abnormal).

In the example shown in FIG. 3, the set of electrodes 24 includes electrodes 24A, 24B, 24C, and 24D, and the set of electrodes 26 includes electrodes 26A, 26B, 26C, and 26D. Processor 40 also controls switch module 48 to apply the stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 46 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 44 is coupled to electrodes 24, 26 via switch module 46 and conductors within leads 20. In some examples, however, IMD 16 does not include switch module 46.

Stimulation generator 44 may be a single channel or multi-channel stimulation generator. In particular, stimulation generator 44 may be capable of delivering a single stimulation pulse, multiple stimulation pulses, or a continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12. In other examples, each electrode may be coupled to a current source and sink, thus allowing individual control of each electrode to achieve the desired current balance. Electrical stimulation may be delivered via combination of two or more electrodes by controlling the current that is sourced or sunk via each of the electrodes. The amount of stimulation current sourced or sunk by an electrode may be programmed to achieve the desired overall effect and a more precise current control or voltage compliance.

In some examples, processor 40 may dynamically change the selected combinations of electrodes 24, 26, i.e., the sensing electrode combination, based on one or more frequency domain characteristics of bioelectrical signals sensed within brain 28, as described in more detail below. Sensing module 46, under the control of processor 40, may sense bioelectrical brain signals and provide the sensed bioelectrical brain signals to processor 40. Processor 40 may control switch module 48 to couple sensing module 46 to a selected combinations of electrodes 24, 26, i.e., a sense electrode combination. In this way, IMD 16 is configured such that sensing module 46 may sense bioelectrical brain signals with a plurality of different sense electrode combinations. Switch module 48 may be electrically coupled to the selected electrodes 24, 26 via the conductors within the respective leads 20, which, in turn, deliver the bioelectrical brain signal sensed across the selected electrodes 24, 26 to sensing module 46. The bioelectrical brain signal may include electrical signals that are indicative of electrical activity within brain 28 of patient 12.

Although sensing module 46 is incorporated into a common housing with stimulation generator 44 and processor 40 in FIG. 3, in other examples, sensing module 46 may be in a separate housing from IMD 16 and may communicate with processor 40 via wired or wireless communication techniques. Example bioelectrical brain signals include, but are not limited to, a signal generated from local field potentials (LPFs) within one or more regions of brain 28 via electrodes deployed in those regions, e.g., in unipolar or bipolar sensing. EEG, ECoG and LFPs are some examples of electrical oscillatory activities that may be measured within brain 28. Non-electrical oscillatory signals may be also utilized (e.g., extra or intracellular biochemical signals or other physiological variables).

Processor 40 may analyze a plurality of bioelectrical brain signals, e.g., by determining relative values of signal characteristics (e.g., potentials or frequency domain characteristics) of the bioelectrical signal, to evaluate different stimulation electrode combinations. A stimulation electrode combination may be associated with a sense electrode combination in memory 42. In some examples, processor 40 may control therapy delivered by stimulation electrode combinations by, at least in part, sensing bioelectrical brain signals with one or more of the sense electrode combinations associated with a respective one of the stimulation electrode combinations and analyzing a frequency domain characteristic of the sensed bioelectrical brain signals. For example, processor 40 may determine an oscillatory behavior of neural activity of a brain site based on frequency domain characteristic, e.g., phase, or based on time domain characteristic, e.g., frequency or voltage amplitude, based on bioelectrical signals sensed by two or more sense electrodes, and compare the relative values of the signals sensed by a plurality of sense electrode combinations, and determine the oscillatory behavior of the brain site neural activity based on the relative values of the signals. Processor 40 may compare the determined oscillatory behavior to a normal or stable behavior associated with the brain site to determine whether the determined behavior deviates from the normal or stable behavior. The determined oscillatory behavior and the normal or stable behavior may be compared by way of comparing the trajectories of the plots of the signals associated with each. In one example, if the determined oscillatory behavior deviation is indicative of a condition that requires correction, processor 40 may control stimulation generator 44 to deliver stimulation via the appropriate stimulation electrode combinations to deliver therapy to the brain site associated with the condition, to shift the associated behavior from the abnormal state to the normal or stable state.

A frequency domain characteristic of the biosignal may include, for example, a phase of a sensed signal, a power level (or energy) within one or more frequency bands of the biosignal, a ratio of the power level in two or more frequency bands, a correlation in change of power between two or more frequency bands, a pattern in the power level of one or more frequency bands over time, and the like. In some examples, processor 40 may adjust a previously selected sensing electrode combination (e.g., by changing a polarity of an electrode of the combination or by adding or removing an electrode from the combination) or otherwise select a sensing electrode combination by selecting a sensing electrode combination that is associated with one or more sense electrodes that provide measurements of oscillatory activity with the highest fidelity or resolution (e.g., oscillatory activity with the highest oscillation amplitude or most stable phase reference point) compared to the other sensed bioelectrical brain signals. In other examples, processor 40 may select a stimulation electrode combination that is associated with the sense electrode combination used to measure signals of neural activity of the target tissue site.

In some examples, processor 40 implements algorithm 60 stored by memory 42 in order to determine which individual sense electrodes are located relative to a target tissue site such that a measure of neural activity in the target tissue site yields ranges that exhibit functional meaning and a high resolution of the oscillation pattern. Processor 40 may then select the most effective sense electrode combination for a target tissue site to determine the oscillatory behavior of the neural activity of the site. Processor 40 may also select a stimulation electrode combination based on the sense electrodes to provide therapy to the target tissue site based on the determined oscillatory behavior. In some examples, algorithm 60 includes instructions that cause processor 40 to determine and analyze oscillatory patterns associated with signals measured by the sense electrodes to determine whether the patterns indicate the presence of a condition associated with a disorder and whether corrective action is needed to shift the behavior of the neural activity of the associated tissue site to a normal or stable state. Processor 40 implements algorithm 60 to determine whether therapy is needed and if so, selects the appropriate stimulation electrode combination and the appropriate parameters to provide therapy for the condition associated with the sensed oscillatory behavior to shift the neural activity to the normal or stable state.

Telemetry module 50 supports wireless communication between IMD 16 and an external programmer 14 or another computing device under the control of processor 40. Processor 40 of IMD 16 may receive, as updates to programs, values for various stimulation parameters such as amplitude and electrode combination, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by radiofrequency (RF) communication techniques. In addition, telemetry module 50 may communicate with external medical device programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Throughout the disclosure, a group of electrodes may refer to any electrodes located at the same position along the longitudinal axis of one or more leads. A group of electrodes may include one electrode or a plurality of electrodes (e.g., two or more electrodes).

Figure 4:
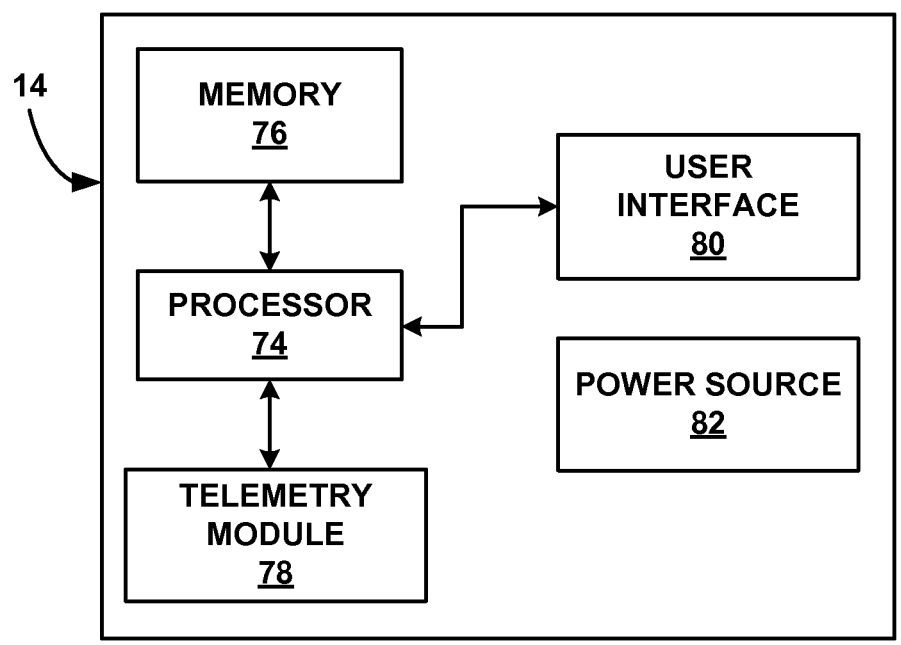
FIG. 4 is a functional block diagram illustrating components of an example medical device programmer suitable for use with the medical device of FIG. 2.

FIG. 4 is a conceptual block diagram of an example external medical device programmer 14, which includes processor 74, memory 76, telemetry module 78, user interface 80, and power source 82. Processor 74 controls user interface 80 and telemetry module 78, and stores and retrieves information and instructions to and from memory 76. Programmer 14 may be configured for use as a clinician programmer or a patient programmer. Processor 74 may comprise any combination of one or more processors including one or more microprocessors, DSPs, ASICs, FPGAs, or other equivalent integrated or discrete logic circuitry. Accordingly, processor 74 may include any suitable structure, whether in hardware, software, firmware, or any combination thereof, to perform the functions ascribed herein to processor 74.

A user, such as a clinician or patient 12, may interact with programmer 14 through user interface 80. User interface 80 includes a display (not shown), such as a LCD or LED display or other type of screen, to present information related to the therapy, such as information related to bioelectrical signals sensed via a plurality of sense electrode combinations. In addition, user interface 80 may include an input mechanism to receive input from the user. The input mechanisms may include, for example, buttons, a keypad (e.g., an alphanumeric keypad), a peripheral pointing device or another input mechanism that allows the user to navigate though user interfaces presented by processor 74 of programmer 14 and provide input.

If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or a finger to provide input to the display. In other examples, user interface 80 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 74 of programmer 14. For example, in some examples, processor 74 may receive a bioelectrical brain signal from IMD 16 or from a sensing module that is separate from IMD 16. The separate sensing module may, but need not be, implanted within patient 12. In some examples, processor 74 may select one or more sensing electrode combinations to acquire characteristics associated with neural activity of a target tissue site such as, for example, an oscillatory pattern to determine whether a condition associated with a disorder is exhibiting abnormal behavior in the monitored site. Processor 74 may also select one or more stimulation electrode combinations to provide DBS to sites in the brain that may require therapy to correct a condition such as, for example, a sensed abnormal oscillatory pattern.

Processor 74 may select a stimulation electrode combination for IMD 16 based on the analysis of the frequency domain characteristics of the sensed bioelectrical brain signals, e.g., by implementing an algorithm similar or identical to that implemented by IMD 16 and stored by memory 42 of IMD 16. Example algorithms are described below with respect to FIGS. 5 and 6. In some examples, e.g., after determining a stimulation electrode combination is desirable based on an observed characteristic of neural activity of a target tissue site such as, for example, an oscillatory activity associated with a condition or disorder requiring therapy, processor 74 may transmit a signal to IMD 16 to instruct IMD 16 to switch stimulation electrode combinations or change stimulation parameters associated with the stimulation electrode combination to provide the appropriate therapy based on the observed activity.

Processor 40 of IMD 16 may receive the signal from programmer 14 via its respective telemetry module 50 (FIG. 3). Processor 40 of IMD 16 may determine based on the received signal the behavior (e.g., an oscillatory pattern) of neural activity associated with the target tissue site as sensed by the sensing electrodes. Processor 40 may also compare the oscillatory pattern to an oscillatory pattern associated with a normal or stable state of the neural activity to determine whether the sensed pattern deviates from the normal or stable state, possibly indicating that a disorder, e.g., a movement disorder, is exhibiting abnormal behavior. In some examples, processor 40 may determine based on the comparison to provide therapy to the target tissue site to shift any sensed abnormal patterns associated with the disorder to a normal or stable state by, for example, switching stimulation electrode combinations by selecting or modifying a stored therapy program from memory 42. In another example, processor 74 of programmer 14 may select a therapy program or a specific stimulation electrode combination and transmit a signal to IMD 16, where the signal indicates the therapy parameter values to be implemented by IMD 16. The indication may be, for example, an alphanumeric identifier or symbol that is associated with the therapy program in memory 42 of IMD 16.

Memory 76 may include instructions for operating user interface 80 and telemetry module 78, and for managing power source 82. Memory 76 may also store any therapy data retrieved from IMD 16 during the course of therapy. The clinician may use this therapy data to determine the progression of the patient condition in order to predict future treatment. Memory 76 may include any volatile or nonvolatile memory, such as RAM, ROM, EEPROM or flash memory. Memory 76 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 78. Accordingly, telemetry module 78 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 82 delivers operating power to the components of programmer 14. Power source 82 may include a battery and a power generation circuit to produce the operating power. In some examples, the battery may be rechargeable to allow extended operation. Recharging may be accomplished by electrically coupling power source 82 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 82 may include circuitry to monitor power remaining within a battery. In this manner, user interface 80 may provide a current battery level indicator or low battery level indicator when the battery needs to be replaced or recharged. In some cases, power source 82 may be capable of estimating the remaining time of operation using the current battery.

Figure 5:
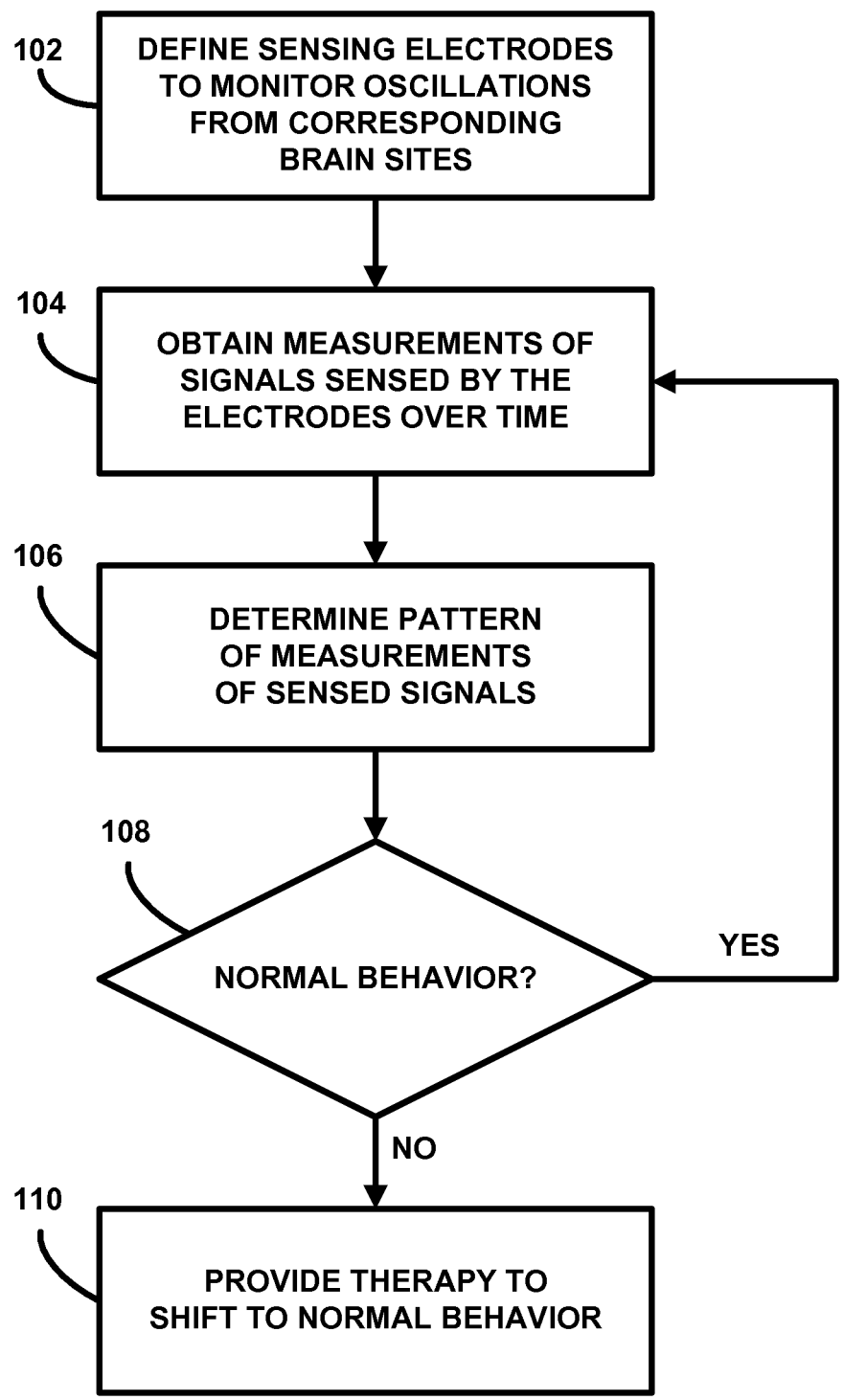
FIG. 5 is a flow diagram of an example technique for determining oscillatory behavior within brain neural networks.

FIG. 5 is a flow diagram of an example technique that processor 40 of IMD 16, processor 74 or programmer 14, or another computing device can implement to monitor behavior of neural activity within brain neural networks. Two or more DBS electrodes may be defined as sensing electrodes and used to monitor neural activity from the brain sites with which they are associated (102). Each of the DBS electrodes may be part of a unipolar or a bipolar sensing electrode pair. In one example, the electrodes may be spatially distinct, such that signals detected by the electrodes may have phase differences such that analysis of the signals by an associated processor may enable characterization of the signals for monitoring and therapeutic purposes. For example, a signal originating from one part of the brain may be detected by the two or more sensing electrodes, and as a result, each of the sensing electrodes may detect the signal from two or more different perspectives, therefore, obtaining two or more different versions of the signal. A relationship between the two or more obtained signals may be defined based on the phase difference between the two or more signals. Measurements may be obtained from the two or more sensing electrodes over a period to time (104). The measurements may be, for example, absolute instantaneous amplitude of voltage of the signals, a frequency of the signals, and the like. The processor may determine a pattern associated with the signals based on the measurements and may determine the relationship between the two or more signals.

In the example of two electrodes, the two signals may be represented by X and Y, and their pattern may be expressed as a relationship of Y versus X as described above with reference to FIG. 1 (106). As measurements are obtained over time, a model for the limit cycle of the oscillatory behavior may be monitored and analyzed to determine whether the neural network exhibits a normal/stable behavior or an abnormal behavior (108). In one example, if the pattern associated with the relationship between X and Y is similar to that of an abnormal behavior of neural activity, e.g., a pattern associated with a movement disorder, then the processor determines that the neural activity is exhibiting an abnormal behavior, and based on the characteristics of the pattern, the processor may instruct the IMD to provide therapy to shift the pattern to one associated with the normal behavior of the neural activity (110). In one example, the processor may dynamically analyze the abnormal pattern to determine details regarding the appropriate therapy, e.g., stimulation therapy parameters, that would shift the pattern from an abnormal behavior to a normal/stable behavior, as explained above with reference to FIG. 1. In one example, if the pattern associated with the relationship between X and Y indicates normal behavior, the processor may terminate the process or reset the process and obtain measurements of the signals by the electrodes (104) at predefined intervals. In this manner, therapy may be dynamically configured and adjusted based on signal patterns sensed by electrodes specific to the patient, therefore, stimulation therapy for the same disorder may vary from one patient to another, and may be patient-specific based on several factors such as, for example, location and/or movement of implanted electrodes, severity of disorder, and the like.

Figure 6:
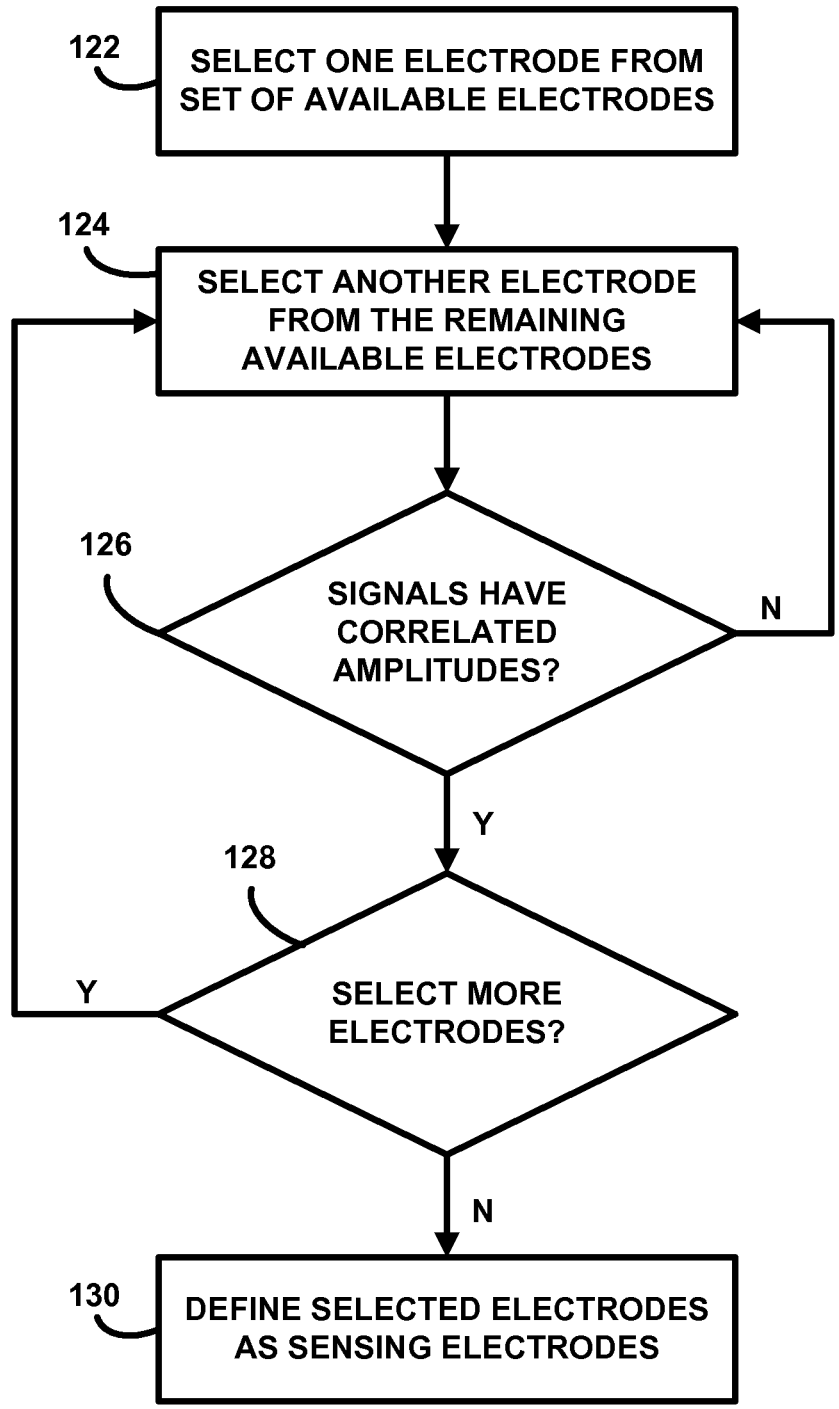
FIG. 6 is a flow diagram of an example technique for determining sensing electrode combinations to use in monitoring oscillatory behavior within brain neural networks.

FIG. 6 is a flow diagram of an example technique that processor 40 of IMD 16, processor 74 or programmer 14, or another computing device can implement to determine sensing electrode combinations to use in monitoring oscillatory behavior of neural activity within brain networks. Two or more spatially-distinct DBS electrodes may be defined as sensing electrodes and used to monitor neural activity signals from a particular brain site. One electrode may be selected from a plurality of available electrodes to measure a signal of neural activity of the brain site (122). A second electrode may then be selected from the remaining electrodes (124). Brain signals may then be obtained by the selected electrodes and compared to one another to determine whether the obtained signals have correlated amplitude ranges (126). Selecting electrodes with correlated amplitude ranges may provide a meaningful functional observation of neural activity of the brain site, in addition to a high resolution of oscillatory patterns, which may provide a better monitoring of the neural activity of the brain site. In one example, two or more electrodes have correlated amplitude ranges if they have a stable frequency relationship. Some characteristics of a stable frequency relationship may be, for example, a stable phase relationship, or a stable relationship between the paths of the signals associated with the electrodes. In one example, a stable phase relationship may be a relationship where the phase difference between the signals obtained by the electrodes does not change over time. In some examples, a certain margin of change in the phase difference may be tolerated as to be considered "no change," where the margin may be defined by, for example, experience, historical data, statistics of ongoing longer term changes within a specific patient and by correlation with symptoms of the particular disease or disorder.

If the second selected electrode is not an appropriate combination with the already-selected electrode, i.e., they do not have correlated amplitude ranges, another electrode may be selected from the remaining available electrodes (124). A determination is made with the newly selected electrode as to whether signals obtained by all selected electrodes have correlated amplitude ranges (126).

If the second selected electrode is an appropriate combination with the already-selected electrode, i.e., they have correlated amplitude ranges, a decision may be made as to whether more electrodes are needed for the sensing electrode combination (128). If another electrode is to be selected, the processor may select another electrode from the remaining available electrodes (124), and a determination may be made as to whether the selected electrode and the already-selected electrodes have correlated amplitude range (126). This may be repeated until there are no more electrodes or if another electrode is not to be selected. If no more electrodes are to be selected, the selected electrodes may be stored as the sensing electrode combination for the associated brain site (130).

While the techniques of this disclosure are described in the context of brain neural network activity, it should be understood that the techniques of this disclosure are applicable to functions of other regions and organs in the body. For example, cardiac functions may be monitored using techniques of this disclosure to determine occurrence of events such as, for example, arrhythmias. In one example, functions of the heart may be monitored and may result in a stable oscillatory trajectory, i.e., the plot of the monitored signal resembles an identifiable shape or circle back to the starting point. Trajectory changes may be a move to non-oscillatory state indicating, for example, an increase in frequency, which may indicate occurrence of fibrillation of the heart. Based on this determination, the system may be moved from the non-oscillatory state to the oscillatory state to restore the heart function to a normal state.

While the examples of this disclosure are described in the context of bioelectrical signals, it should be understood that the techniques of this disclosure may be utilized with other types of signals. For example, as mentioned above, concentrations of chemicals in the brain may be measured to obtain biochemical signals. The relationship between the concentration of chemicals and certain diseases or functions of certain organs may be examined to determine chemical levels associated with normal functions/activities and chemical levels associated with abnormal functions/activities, and to control therapy provided to achieve the desired chemical levels. This example may be applicable to diseases or conditions associated with organs that release certain chemicals in the body, for example. Other relationships may also be examined, such as, for example, effects of the functions of one organ or part of the body, on another organ or part of the body, and the implications of that relationship on a disease or condition. In other examples, a relationship may be determined between a bioelectrical or biochemical signal and a mechanical response (e.g., a specific patient behavior or reaction), such that certain bioelectrical signals or chemical levels in a body part or organ may have a relationship to a certain behavior, where maintaining a certain bioelectrical or biochemical level ensures a desired patient behavior, for example.

The techniques described in this disclosure, including those attributed to programmer 14, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 40 of IMD 16 and/or processor 74 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples of the disclosure have been described. These and other examples are within the scope of the following claims.

The invention claimed is:

1. A method comprising:
receiving, with a processor, a first bioelectrical signal sensed at a first location within a brain of a patient;
receiving, with the processor, a second bioelectrical signal sensed at a second location within the brain of the patient, wherein the first and second locations are spatially distinct;
determining, with the processor, a limit cycle plot of the first and second bioelectrical signals, wherein the limit cycle plot is indicative of a trajectory of the first and second bioelectrical signals;
determining, with the processor, that the brain is in a first state based on the limit cycle plot; and
controlling delivery of therapy to the patient based on determining that the brain is in the first state, wherein controlling delivery of therapy to the patient comprises selecting the therapy to produce a second state in the brain.

2. The method of claim 1, wherein the therapy comprises at least one of electrical stimulation therapy or drug-delivery therapy.

3. The method of claim 1, wherein determining the limit cycle plot of the first and second bioelectrical brain signals comprises generating the limit cycle plot based on the first and second bioelectrical brain signals.

4. The method of claim 1, wherein the limit cycle plot comprises a first limit cycle plot, and wherein determining that the brain is in the first state based on the limit cycle plot comprises comparing the first limit cycle plot to a second limit cycle plot and determining that the brain is in the first state based on the comparison.

5. The method of claim 1, wherein determining that the brain is in a first state based on the limit cycle plot comprises determining that the limit cycle plot takes a predetermined shape.

6. The method of claim 5, wherein the predetermined shape comprises a circle.

7. The method of claim 1, wherein the limit cycle plot illustrates a parameter defining the first bioelectrical signal plotted versus the parameter defining the second bioelectrical signal.

8. The method of claim 7, wherein the parameter comprises at least one of an amplitude, a frequency, a phase, a power level within one or more frequency bands, a ratio of a power level within one or more frequency bands, or a pattern in a power level within one or more frequency bands.

9. The method of claim 1, wherein the limit cycle plot comprises a limit cycle plot indicative of a first trajectory of the first and second bioelectrical signals, and wherein selecting the therapy to produce the second state in the brain comprises selecting the therapy to produce a second trajectory of the first and second bioelectrical brain signals.

10. The method of claim 9, wherein the first trajectory is indicative of an abnormal brain state and the second trajectory is indicative of a normal brain state.

11. A system comprising:
a sensing module configured to sense a first bioelectrical signal at a first location within a brain of a patient and a second bioelectrical signal at a second location within the brain of the patient, wherein the first and second locations are spatially distinct; and
a processor configured to determine a limit cycle plot of the first and second bioelectrical signals, wherein the limit cycle plot is indicative of a trajectory of the first and second bioelectrical signals, determine that the brain is in a first state based on the limit cycle plot, and control delivery of therapy to the patient based on determining that the brain is in the first state, by at least selecting the therapy to produce a second state in the brain.

12. The system of claim 11, further comprising an implantable medical device configured to deliver the therapy, wherein the therapy comprises at least one of electrical stimulation therapy or drug-delivery therapy.

13. The system of claim 11, wherein the processor is configured to determine the limit cycle plot of the first and second bioelectrical brain signals by at least generating the limit cycle plot based on the first and second bioelectrical brain signals.

14. The system of claim 11, wherein the limit cycle plot comprises a first limit cycle plot, and wherein the processor is configured to determine that the brain is in the first state based on the limit cycle plot by at least comparing the first limit cycle plot to a second limit cycle plot and determining that the brain is in the first state based on the comparison.

15. The system of claim 11, wherein the processor is configured to determine that the brain is in a first state based on the limit cycle plot by at least determining that the limit cycle plot takes a predetermined shape.

16. The system of claim 15, wherein the predetermined shape comprises a circle.

17. The system of claim 11, wherein the limit cycle plot illustrates a parameter defining the first bioelectrical signal plotted versus the parameter defining the second bioelectrical signal.

18. The system of claim 17, wherein the parameter comprises at least one of an amplitude, a frequency, a phase, a power level within one or more frequency bands, a ratio of a power level within one or more frequency bands, or a pattern in a power level within one or more frequency bands.

19. The system of claim 11, wherein the limit cycle plot comprises a limit cycle plot indicative of a first trajectory of the first and second bioelectrical signals, and wherein the processor is configured to select the therapy to produce a second state in the brain by at least selecting the therapy to produce a second trajectory of the first and second bioelectrical brain signals.

20. The system of claim 19, wherein the first trajectory is indicative of an abnormal brain state and the second trajectory is indicative of a normal brain state.

21. A non-transitory computer-readable medium comprising instructions that, upon execution, cause a programmable processor to:
receive a first bioelectrical signal sensed at a first location within a brain of a patient;
receive a second bioelectrical signal sensed at a second location within the brain of the patient, wherein the first and second locations are spatially distinct;
determine a limit cycle plot of the first and second bioelectrical signals, wherein the limit cycle plot is indicative of a trajectory of the first and second bioelectrical signals;
determine that the brain is in a first state based on the limit cycle plot; and
control delivery of therapy to the patient based on determining that the brain is in the first state by at least selecting the therapy produce a second state in the brain.

22. The non-transitory computer-readable medium of claim 21, wherein the limit cycle plot comprises a first limit cycle plot, and wherein the instructions cause the programmable processor to determine that the brain is in a first state based on the limit cycle plot by at least comparing the first limit cycle plot to a second limit cycle plot and determining that the brain is in the first state based on the comparison.

23. The non-transitory computer-readable medium of claim 21, wherein the instructions cause the programmable processor to determine that the brain is in the first state based on the limit cycle plot by at least determining that the limit cycle plot takes a predetermined shape.

24. The non-transitory computer-readable medium of claim 21, wherein the limit cycle plot comprises a limit cycle plot indicative of a first trajectory of the first and second bioelectrical signals, and wherein the instructions cause the programmable processor to select the therapy to produce a second state in the brain by at least selecting the therapy to produce a second trajectory of the first and second bioelectrical brain signals.

25. A system comprising:
means for receiving a first bioelectrical signal sensed at a first location within a brain of a patient;
means for receiving a second bioelectrical brain signal sensed at a second location within the brain of the patient, wherein the first and second locations are spatially distinct;
means for determining a limit cycle plot of the first and second bioelectrical signals, wherein the limit cycle plot is indicative of a trajectory of the first and second bioelectrical signals;
means for determining that the brain is in a first state based on the limit cycle plot; and
means for controlling delivery of therapy to the patient based on determining that the brain is in the first state, wherein the means for controlling delivery of therapy comprises means for selecting the therapy to produce a second state in the brain.

26. The system of claim 25, wherein the limit cycle plot comprises a first limit cycle plot, and wherein the means for determining that the brain is in the first state determines that the brain is in the first state based on the limit cycle plot by at least comparing the first limit cycle plot to a second limit cycle plot and determining that the brain is in the first state based on the comparison.

27. The system of claim 25, wherein the means for determining that the brain is in a first state determines that the brain is in the first state based on the limit cycle plot by at least determining that the limit cycle plot takes a predetermined shape.

28. The system of claim 25, wherein the limit cycle plot comprises a limit cycle plot indicative of a first trajectory of the first and second bioelectrical signals, and wherein the means for selecting the therapy selects the therapy to produce a second state in the brain by at least selecting the therapy to produce a second trajectory of the first and second bioelectrical brain signals.

* * * * *